United States Patent [19]
Chin et al.

[11] Patent Number: 5,195,533
[45] Date of Patent: Mar. 23, 1993

[54] BIOPSY NEEDLE INSTRUMENT FOR STORING MULTIPLE SPECIMENS

[75] Inventors: Yem Chin, Burlington; Michael S. H. Chu, Brookline, both of Mass.

[73] Assignee: Boston Scientific Corporation, Watertown, Mass.

[21] Appl. No.: 881,028

[22] Filed: May 8, 1992

[51] Int. Cl.⁵ .................................... A61B 10/00
[52] U.S. Cl. ............................. 128/754; 128/751; 128/749; 606/167; 606/170
[58] Field of Search .............. 128/754, 744, 751; 606/167, 168, 170

[56] References Cited

U.S. PATENT DOCUMENTS

| | | | |
|---|---|---|---|
| 4,766,907 | 8/1988 | de Groot et al. | 128/751 |
| 4,776,346 | 10/1988 | Beraha et al. | 128/754 |
| 4,790,329 | 12/1988 | Simon | 128/754 |
| 4,799,495 | 7/1991 | Simon | 128/754 |
| 4,893,635 | 1/1990 | de Groot et al. | 128/754 |
| 4,917,100 | 4/1990 | Nottke | 128/749 |
| 4,958,625 | 9/1990 | Bates | 128/754 |
| 4,976,269 | 12/1990 | Mehl | 128/754 |
| 5,031,634 | 7/1991 | Simon | 128/754 |
| 5,056,529 | 10/1991 | de Groot | 606/170 |

Primary Examiner—Stephen C. Pellegrino
Assistant Examiner—Gary Jackson
Attorney, Agent, or Firm—Pearson & Pearson

[57] ABSTRACT

A biopsy needle instrument for capturing a plurality of sequentially biopsied, discrete specimens. The instrument includes a housing, an axially elongated stylet and a cannula coaxially disposed about the stylet. The stylet and cannula have distal and proximal ends and extend from the housing. The stylet and cannula can move relative to each other and to the housing between retracted and extended positions. The stylet includes a side-facing notch adjacent the distal end of the stylet having an axial length that is greater than a predetermined specimen length. Portions of the cannula adjacent the distal end overlie the side-facing notch when the cannula and stylet are both retracted. When the stylet is extended and the cannula is retracted, a distal portion of the notch having length corresponding to the predetermined specimen length is disposed for facilitating the prolapse of tissue into the notch.

19 Claims, 4 Drawing Sheets

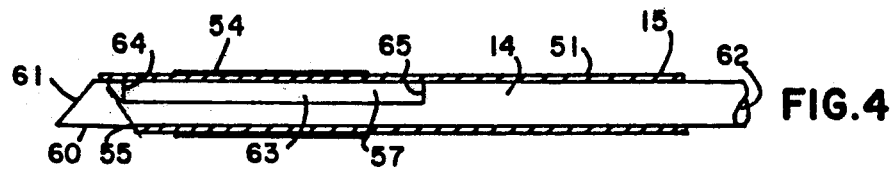
FIG. 4
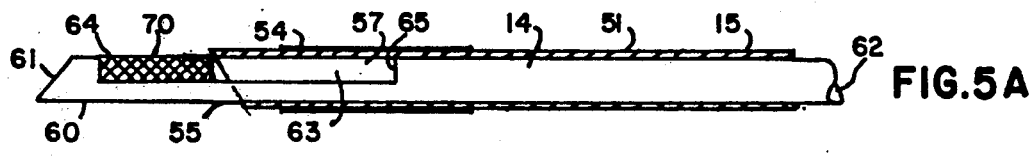
FIG. 5A
FIG. 5B
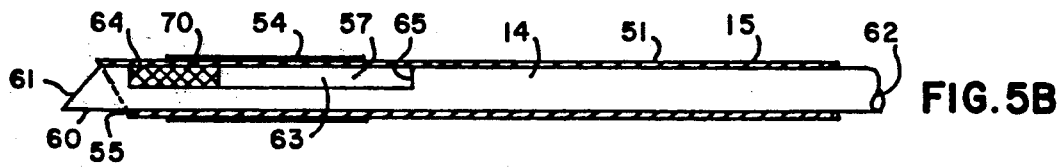
FIG. 6A
FIG. 6B
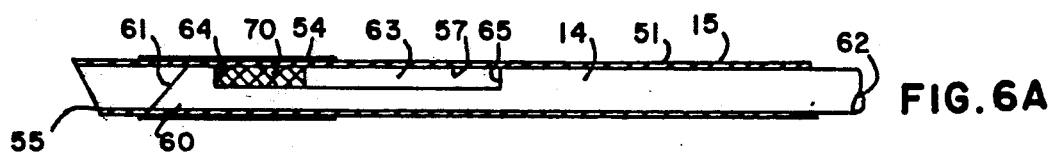
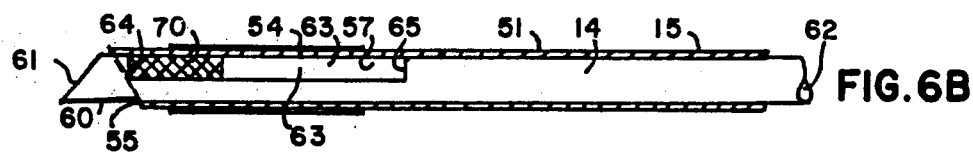
FIG. 7A
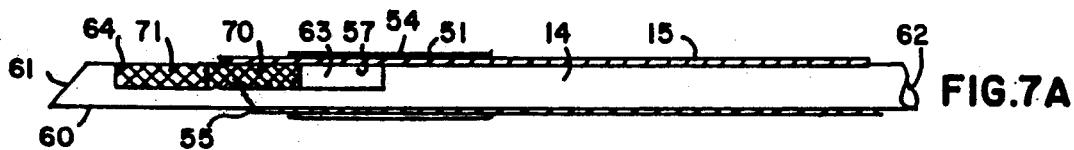
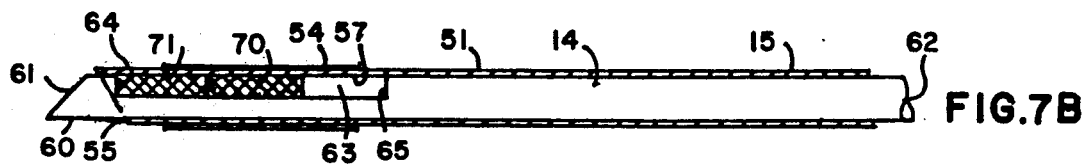
FIG. 7B

BIOPSY NEEDLE INSTRUMENT FOR STORING MULTIPLE SPECIMENS

BACKGROUND OF THE INVENTION

1. Field of the Invention

This invention generally relates to surgical biopsy instruments and more specifically to a method and apparatus for capturing multiple biopsies in such instruments.

2. Description of Related Art

A biopsy needle instrument is frequently used to obtain a tissue specimen for microscopic examination to determine malignancy, while subjecting the patient to the least trauma. Typically, the instrument consists of a long, thin probe, termed a stylet, within a close-fitting hollow needle, termed a cannula. A firing device first projects the stylet into the tissue, followed immediately by the cannula. The stylet has a notch into which tissue will prolapse when the stylet enters the tissue. As the cannula subsequently slides over the stylet, it severs the prolapsed tissue from the surrounding mass and captures the prolapsed tissue as a specimen within the notch. The instrument then is typically withdrawn and the piece of tissue removed from the stylet.

U.S. Letters Patent No. 4,958,625 of Bates et al that issued Sept. 25, 1990 for a Biopsy Needle Instrument (assigned to the same assignee as the present invention) discloses a biopsy instrument needle that extends the stylet and the cannula when a firing button is pushed. A physician cocks a firing mechanism by retracting the cannula and the stylet individually into latched, spring-loaded positions. After orienting the distal end of the biopsy needle instrument, the physician activates the firing button. The stylet latch releases. As the stylet extends into the tissue, a portion of that tissue prolapses into a side-facing notch as a specimen. When the stylet reaches its extended position, it releases a cannula latch. The cannula slides over the stylet and severs the prolapsed tissue in the notch from any surrounding tissue and covers the notch thereby capturing the specimen. Next the physician removes the entire needle assembly from the patient and then extracts the biopsy specimen from the notch before another specimen can be taken.

In the foregoing patent, the cannula has a one-piece construction. As an alternative, the cannula can comprise two axially aligned tubular sections joined by a releasable fitting such as a Luer-lock fitting. In this configuration a distal cannula section constitutes a removable sheath that can be positioned independently of the remaining portions of the instrument. This is particularly useful for verifying instrument placement by various imaging means. Once the orientation is verified, the physician can reinsert the end of the stylet through the sheath and lock the two cannula sections together prior to taking a specimen. The removable sheath also facilitates the extraction of a specimen from the notch as its removal provides unobstructed access to the notch.

In many situations it is desirable to obtain plural tissue specimens either by repositioning or relocating the biopsy needle. Relocating the biopsy needle involves the withdrawal of the needle from the immediate tissue mass for insertion in other tissue without withdrawing the needle from the patient. Repositioning the biopsy needle involves the complete withdrawal of the needle from the patient. When the foregoing biopsy instrument needle is used without a removable sheath, it is not possible to relocate the needle. If a removable sheath is used, relocation is possible. However, it is necessary to completely withdraw the needle from the sheath after each biopsy in order to extract and identify each specimen. Consequently, prior art biopsy needle instruments effectively require repositioning for each biopsy even when the instrument includes a removable sheath. This repositioning process can be time consuming and it complicates biopsy procedures. Even if a two-piece cannula is used, the requirement for reattaching the needle instrument with its integral cannula section to the detached cannula section further complicates the biopsy procedures.

SUMMARY

Therefore it is an object of this invention to provide a biopsy needle instrument and biopsy method for capturing multiple specimens in sequence.

Another object of this invention is to provide a biopsy needle instrument and biopsy method for capturing multiple specimens without the requirement for unloading the specimens.

Still another object of this invention is to provide a biopsy needle instrument and biopsy method for capturing multiple specimens in sequence without the necessity for completely removing the biopsy needle from the patient.

Yet another object of this invention is to provide a small and compact and, therefore, less traumatic biopsy needle instrument for capturing multiple specimens.

Still yet another object of this invention is to provide a biopsy needle instrument and biopsy method for capturing multiple specimens in a relatively easy and efficient fashion.

In accordance with one aspect of this invention, a biopsy needle instrument includes a housing, an axially-elongated stylet extending from the housing and a cannula coaxially extending from the housing and disposed about the stylet means. The stylet and cannula can move relative to each other and to the housing between extended and retracted positions. The stylet and cannula define, during a given operation, a specimen of a predetermined specimen axial length. The stylet includes means coacting with the cannula for storing multiple, sequentially obtained specimens within the instrument.

In accordance with another aspect of this invention, a biopsy needle instrument captures a plurality of sequentially biopsied, discrete specimens, each of a predetermined specimen length. The instrument includes a housing, an axially elongated stylet that extends from the housing with distal and proximal ends and a cannula coaxially disposed about the stylet. A displacement mechanism in the housing moves the stylet and cannula relative to each other and to the housing between retracted and extended positions. The stylet includes a side-facing notch adjacent the distal end thereof having an axial length that is greater than the predetermined specimen length. Portions of the cannula adjacent the distal end thereof overlie the side-facing notch when the cannula and stylet are both in the retracted or extended positions. The cannula exposes the predetermined length of the notch at the distal end thereof when the cannula and stylet are in their retracted and extended positions respectively. During successive operations, the biopsy specimens transfer along the notch inside the cannula for storage seriatim in the side-facing notch.

In accordance with still another aspect of this invention, a biopsy needle includes an elongated side-facing notch formed in a stylet supported within a cannula. The stylet and cannula are supported for relative independent displacement between retracted and extended positions. When the stylet and cannula are in their extended and retracted positions respectively, the cannula and side-facing notch define a specimen of a predetermined axial length. Thereafter multiple specimens are obtained through an iterative process involving an extension of the cannula over the stylet to sever and cover the specimen, a retraction of the stylet and the cannula and the subsequent advance of the stylet independently of the cannula. During this advance, the specimen at a distal end of the notch displaces proximally along the notch thereby to enable additional tissue to prolapse into the exposed portions of the notch distally located with respect to the cannula during a successive operation.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 4 is a cross-sectional view of a stylet and cannula constructed in accordance with this invention in a retracted position;

FIGS. 5A and 5B depict the stylet and cannula of FIG. 4 during a sequential transfer of the stylet and cannula to extended positions;

FIGS. 6A and 6B depict the retraction of the stylet and cannula shown in FIGS. 5A and 5B; and FIGS. 7A and 7B depict the transfer of the stylet and cannula to the extended position for purposes of obtaining second specimen.

DESCRIPTION OF ILLUSTRATIVE EMBODIMENTS

Figure 1:
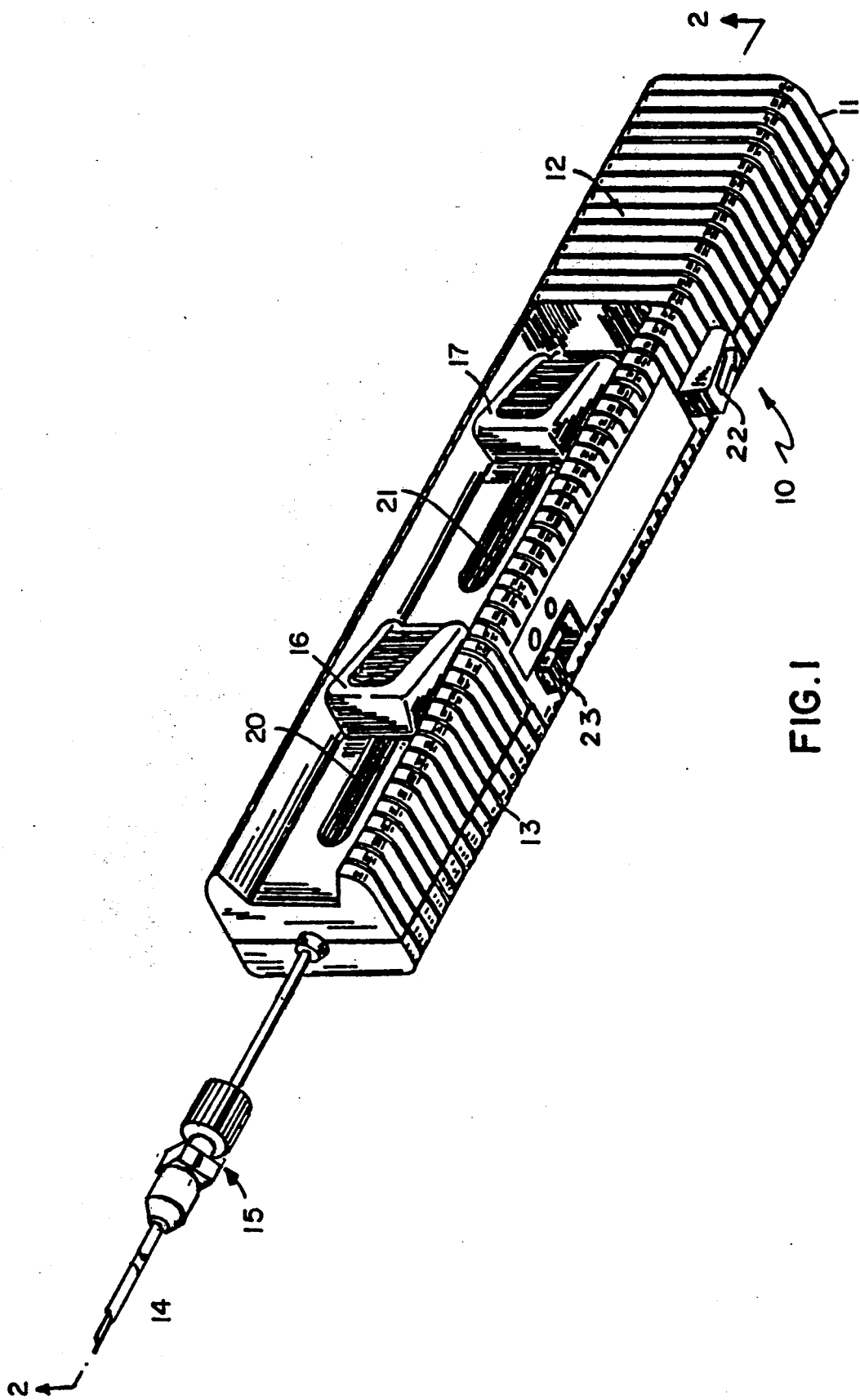
FIG. 1 is a perspective view of an embodiment of a biopsy needle instrument constructed in accordance with this invention.

Referring to FIG. 1, a biopsy instrument needle 10 of this invention has a housing 11 including an upper housing 12 and a lower housing 13. A stylet 14 and cannula 15 project from the housing 11. A forward loading slide switch 16 and a rearward loading slide switch 17 protrude from the upper housing 12 and are constrained to move axially within slots 20 and 21 respectively. A firing button 22 and a selector switch 23 also project from the housing 11.

When the stylet 14 is to be loaded for firing, the rear loading slide switch 17 attached to the stylet 14 slides rearwardly or to the right within the slot 21 to the position shown in FIG. 1. When the stylet 14 is fired, the rear loading slide switch 17 moves forward (or to the left in FIG. 1) in the slot 21.

Similarly, when the cannula 15 is to be loaded for firing, the forward loading slide switch 16 that attaches to the cannula 15, slides rearwardly within the slot 20 (again to the right to the position shown in FIG. 1). When the cannula 15 is fired, the forward slide switch 16 moves forward (to the left) within the slot 20.

Figure 2:
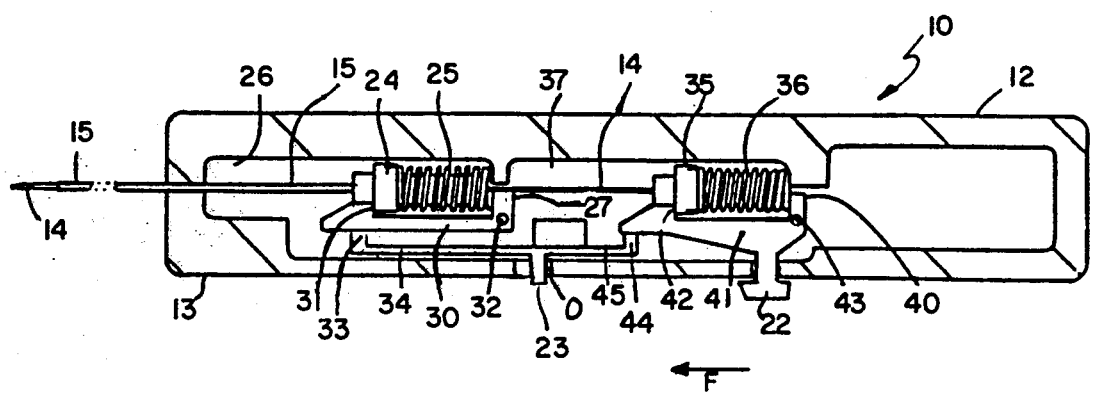
FIG. 2 is a cross-sectional view taken generally along lines 2—2 in FIG. 1.

FIG. 2 shows the instrument firing mechanism positioned within the lower housing 13. The stylet 14 is located coaxially within the cannula 15 and projects through a forward end of the lower housing 13. The rearward end of the cannula 15 attaches to a cannula retaining collar 24 that a spring 25 biases forwardly (Arrow F). The cannula retaining collar 24 and the spring 25 are located within a forward cavity 26 of the lower housing 13. The rearward end of the spring 25 rests against a rear lever 27 of a forward rocker arm 30 and is held in a compressed state by engagement of the cannula retaining collar 24 by a latch portion 31 of the forward rocker arm 30. The forward rocker arm 30 is prevented from pivoting about a pin 32 (thereby releasing the cannula retaining collar 24 and the spring 25) when the selector switch 23 is in the position designated as "O" by a forward restraining projection 33 of a forward arm 34 that forms a part of selector switch 23.

The rearward end of the stylet 14 extends through the cannula 15, the cannula retaining collar 24 and the spring 25 to attach to a stylet retaining collar 35 that a spring 36 biases in the forward direction (Arrow F). The stylet retaining collar 35 and spring 36 are located within a rearward cavity 37 of the lower housing 13. The rearward end of the spring 36 rests against a rear lever 40 of a rearward rocker arm 41 and is held in the compressed state by engagement of the stylet retaining collar 35 by a latch portion 42 of the rearward rocker arm 41. The rearward rocker arm 41 is prevented from pivoting about a pin 43 (and thereby stylet retaining collar 35 and spring 36) when the selector switch 23 is in the position designated as "O" by a rearward restraining projection 44 of a rearward arm 45 of the selector switch 23.

As the selector switch 23 moves forward in the direction of Arrow F, the forward and rearward restraining projections 33 and 44 move forward from the forward rocker arm 46 and rearward rocker 41 respectively. The rearward rocker arm 41 is thus free to pivot counterclockwise about the pin 43 and the forward rocker arm 30 is also free to pivot counterclockwise.

As now will be apparent, the forward slide switch 16 in FIG. 1 engages the cannula restraining collar 24 and, with the latch 30, constitutes a structure for retracting the cannula 15 with respect to the housing 11 into a latched position as shown in FIG. 2 while simultaneously compressing the spring 25. When the latch 30 releases, the spring 25, cannula engaging collar 24 and latch 30 constitute a structure that displaces the cannula 15 to an extended position. Similarly, the rearward slide switch 17 in FIG. 1 attaches to the stylet retaining collar 35 and displaces the stylet to a retracted position while simultaneously compressing the spring 36. When the latch 41 releases the stylet retaining collar 35, the spring 36 and the collar 35 displace the stylet 14 axially to an extended position.

When the instrument is in a cocked position as shown in FIG. 2, pivoting the rearward rocker arm 41 first releases the stylet 14. When the collar 35 reaches its extended position, it engages the rear lever 27 on the forward rocker arm 30 thereby releasing the cannula collar 24. Consequently the structures shown in FIGS. 1 and 2 including the forward and rear slide switches 16 and 17 and the other structures shown in FIG. 2 constitute displacement means that can transfer the stylet and the cannula between extended and retracted positions relative the housing 11 and relative to each other.

Figure 3:
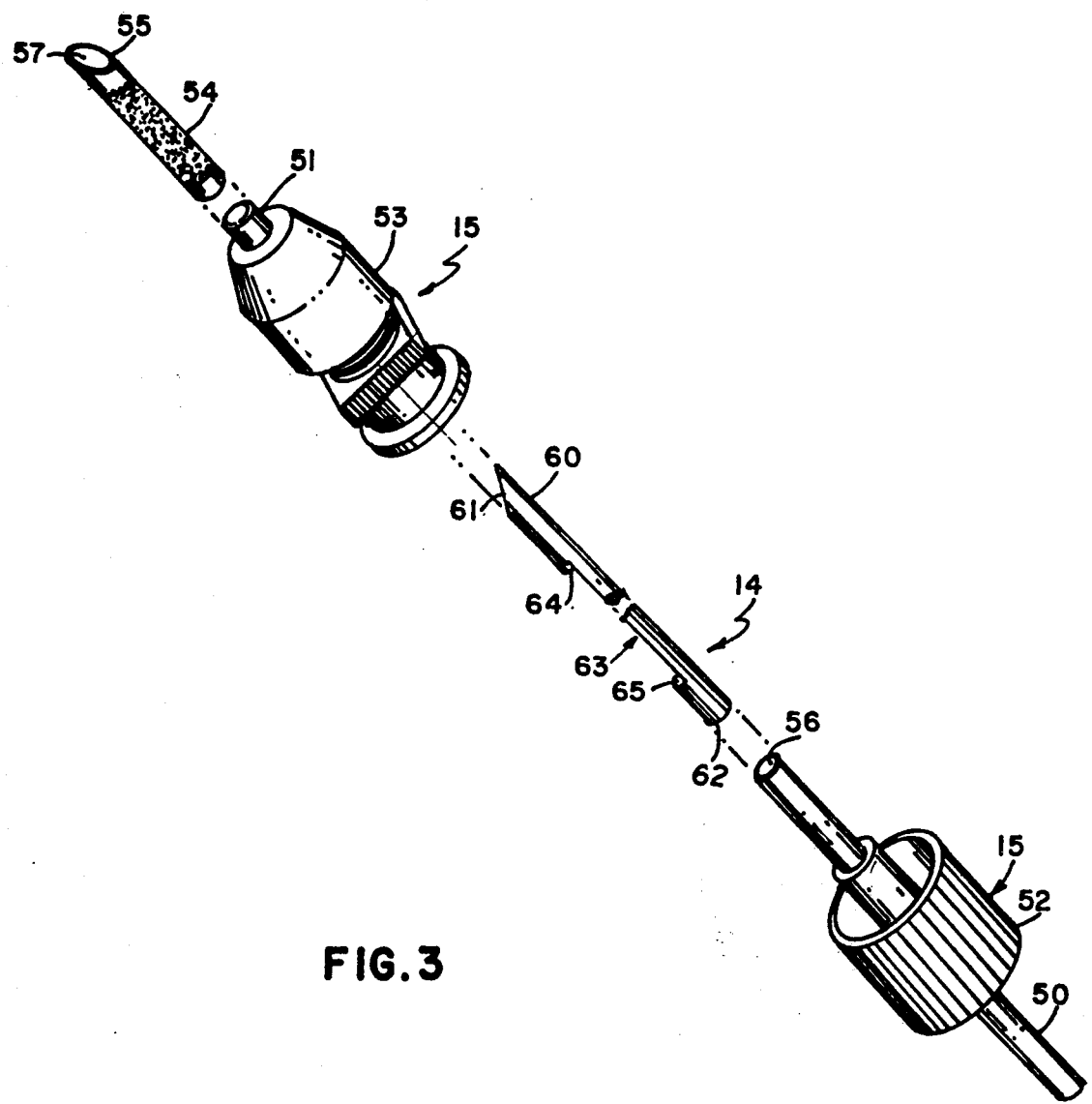
FIG. 3 is an exploded perspective view of portions of a stylet and cannula constructed in accordance with this invention.

FIG. 3 is an exploded view of portions of the cannula 15 and the stylet 14 at a distal position of the instrument 10 shown in FIG. 1. More specifically, the cannula 15 includes a proximal cannula section 50 that connects to the cannula retaining collar 24 in FIG. 2 and a distal cannula section 51. A male Luer-lock fitting 52 at the distal end of the proximal cannula portion 50 mates with a female Luer-lock fitting 53 thereby to provide a releasable fitting between the proximal and distal cannula sections 50 and 51. This facilitates the removal of the distal cannula section 51 that therefore functions as a removable sheath.

Still referring to FIG. 3, the distal cannula section 51 has a marker 54 formed at the distal end thereof to facilitate position verification by various imaging means. The marker 54 can take many forms depending upon the particular imaging modality selected for orienting the instrument.

The end of the distal cannula section 51 terminates distally with a beveled cutting edge 55. A passage 56 through the cannula section 50 and a coaxial passage 57 in the distal cannula section 51 provide a continuous, axially extending passage for the stylet 14.

Still referring to FIG. 3, the distal portion of the stylet 14 includes a distal end 60 and a beveled edge 61. In a preferred form the beveled edge 61 is oppositely facing with respect to the beveled edge 55. A main body portion 62 of the stylet extends through the cannula sections 50 and 51 to attach to the stylet retaining collar 35 shown in FIG. 2.

In accordance with this invention, the distal end position of the stylet 14 has formed therein an elongated notch 63 extending between a distal radial end surface 64 and a proximal end surface 65. The distance between the distal and proximal end surfaces 64 and 65 exceeds the length of a specimen to be gathered. That specimen length corresponds to the axial portion of the notch 63 that extends past the beveled edge 55 when the cannula 15 is retracted and the stylet 14 is extended. The exact increase in length depends upon the number of discrete specimens to be captured in the notch 63.

In one embodiment, for example, the distance between the distal and proximal end surfaces 64 and 65 is three times the predetermined specimen length. Consequently the instrument 10 can readily axially displace three specimens in the notch 63. It also is possible to increase that number of specimens, because the specimens tend to compact as they are captured in the notch 63 without significant commingling of the tissues. For example, it has been possible to capture four to six specimens in a notch having a length equal to three specimen lengths. When the distal cannula section 51 is removed, the successive specimens can be readily removed with the first specimen abutting the proximal end surface 65 and the last obtained specimen abutting the distal end surface 64.

The operation and method by which the instrument disclosed in FIGS. 1 through 3 obtains multiple specimens can be better understood by reference to the sequence of operations depicted in FIGS. 4 through 7B. FIG. 4 shows the stylet 14 and cannula 15 in a cocked condition such as provided when the apparatus in the housing 11 is positioned as shown in FIG. 2. Both the stylet 14 and cannula 15 are in a retracted position.

FIGS. 5A and 5B depict the operating sequence that occurs during firing. When the firing button 22 releases the stylet 14, it snaps to an extended position as shown in FIG. 5A while the cannula 15 remains stationary. This exposes a portion of the notch 63 extending between the beveled cutting edge 55 and the distal end surface 64. When the stylet 14 penetrates tissue, adjacent portions of the tissue prolapse into the exposed portion of the notch 63. Next the cannula 15 snaps to its extended position as shown in FIG. 5B while the stylet 14 remains stationary. As this occurs the beveled cutting edge 55 severs the prolapsed tissue from any surrounding tissue to define a first specimen 70 and captures the specimen 70 in the notch 63 abutting the distal end surface 64.

The physician then can recock the instrument as shown in FIG. 6A to take a successive sample. Specifically the physician retracts the rearward slide switch 17, shown in FIG. 1, to retract the stylet 14 as shown in FIG. 6A. The forward slide switch 16 is displaced to retract the cannula 15 as shown in FIG. 6B. When the system is cocked and ready to fire again, as shown in FIG. 6B, the first specimen 70 generally remains in the notch 63 adjacent the radial end surface 64. The specimen 70 may displace slightly toward the proximal end surface 65 when the cannula 15 retracts, but this displacement does not affect the operation.

When the physician has repositioned the instrument, the physician fires the mechanism by operating the firing button 22. When this occurs, the stylet 14 again snaps from the retracted position shown in FIG. 6B to the extended position shown in FIG. 7A whereupon the first specimen 70 displaces axially toward the proximal end surface 65. This essentially clears that portion of the notch that extends distally of the beveled cutting edge 55 and allows additional tissue to prolapse into the distal portion of the notch 63 as a second specimen 71. Two forces provide this relative displacement of the first specimen 70. First, the spring 36 shown in FIG. 2, drives the stylet 14 at such a high velocity and acceleration that the inertia of the specimen 70 is not overcome; it remains fixed in space. Second some friction between the outer surface of the specimen 70 and inner surface of the cannula 15 tends to hold the specimen 70 in place relative to the cannula. When the operation completes, the cannula 15 moves to its extended position as shown in FIG. 7B. Now the notch 63 captures both the first specimen 70 and the second specimen 71. The specimens are axially aligned in the notch 63 and retain the sequence in which they are obtained.

If another specimen is needed, the physician merely repeats the sequence of FIGS. 6A through 7B. When the stylet 14 snaps from the position shown in FIG. 6B to that shown in FIG. 7A, both the first and second specimens 70 and 71 translate toward the proximal radial surface 65 to permit capture of another specimen.

In summary, a biopsy needle instrument 10 as shown in FIG. 1 and constructed in accordance with this invention can capture multiple specimens taken sequentially from different positions in the body. The instrument severs a specimen taken from surrounding tissue as the cannula 15 moves to an extended position as shown in FIG. 5B. Next the stylet 14 and cannula 15 are retracted as shown in FIGS. 6A and 6B. Then the stylet 14 advances independently of the cannula 15 to define a successive specimen. During this motion any previously obtained specimen remains fixed in its position relative to the cannula.

In accordance with the various objects of this invention, the biopsy instrument needle 10 shown in FIGS. 1 through 3 and operated in accordance with the sequence and method of FIGS. 4 through 7B can capture a plurality of sequentially biopsied, discrete specimens. The specimens are stored axially in the side-facing notch 63 in the order in which they are taken. Consequently, this small and compact structure provides an ability to obtain multiple specimens with less trauma to a patient. Moreover, as the physician must merely displace the forward and rearward slide switches 16 and 17 and activate the selector switch 23 and firing button 22, the instrument is easy to use. Finally it is not necessary to manually unload specimens or remove a needle for each biopsy. Consequently the process for obtaining multiple biopsies is simplified and made more efficient.

This invention has been described in terms of a specific structure. It will be apparent, however, that a number of variations and modifications can be made to this specifically disclosed structure. For example, both the shape and the length of the side-facing notch can be varied. The inner cannula surface overlying the notch might be treated chemically or mechanically to reduce friction. The surface at the notch may be mechanically roughened to increase friction between the specimen and the stylet 14 at the notch so that increased friction exists between the surface of the notch and the specimen that minimizes a tendency of the specimen to displace distally in the notch. The invention is adapted for use in a variety of applications involving stylets and cannula of different diameters. Different structures can be used for producing the relative displacement of the cannula and stylet. Therefore, it is the intent of the appended claims to cover all such variations and modifications as come within the true spirit and scope of this invention.

What is claimed as new and desired to be secured by Letters Patent of the United States is:

1. In a biopsy needle instrument having a housing, axially elongated stylet means extending from said housing at a proximal position for defining a specimen of a predetermined specimen length at a distal position thereof, cannula means coaxially extending from said housing and disposed about said stylet means for severing the defined specimen adjacent said stylet means and displacement means for moving said stylet and cannula means relative to each other and to said housing between extended and retracted positions, the improvement of multiple specimen capture means formed with said stylet means and cooperatively positioned with said cannula means for sequentially obtaining and storing multiple specimens.

2. A biopsy needle instrument as recited in claim 1 wherein said multiple specimen capture means comprises a side-facing notch formed in said stylet means adjacent the distal position thereof having an axial length that is greater than the predetermined specimen length, portions of said cannula adjacent the distal position thereof overlying said side-facing notch when said cannula and stylet means are both in said retracted or extended positions and exposing a portion of said notch adjacent the distal position corresponding to the predetermined specimen length when said cannula and said stylet means are in their retracted and extended positions respectively.

3. A biopsy needle instrument as recited in claim 2 wherein said displacement means extends said stylet and said cannula at a velocity that produces only minimal axial specimen displacement with the moving one of said cannula means and said stylet means.

4. A biopsy needle instrument as recited in claim 3 wherein said cannula means includes marker means at the distal end thereof for facilitating the placement of said instrument.

5. A biopsy needle instrument as recited in claim 2 wherein said cannula means includes distal and proximal sections releasably joined proximally from the position of said side-facing notch and releasable clamping means for joining said sections, said distal section being removable from said instrument to provide access to any specimens stored in said side-facing notch.

6. A biopsy needle instrument as recited in claim 5 wherein said cannula means includes marker means at the distal end thereof for facilitating the placement of said instrument.

7. A biopsy needle instrument for capturing a plurality of sequentially biopsied, discrete specimens, each of a predetermined specimen length, comprising:
   A. a housing,
   B. an axially elongated stylet extending from said housing and having distal and proximal ends,
   C. a cannula coaxially disposed about said stylet and having distal and proximal ends,
   D. displacement means in said housing for moving said stylet and said cannula relative to each other and to said housing between retracted and extended positions,
   E. a side-facing notch formed in said stylet adjacent the distal end thereof with an axial length that is greater than the predetermined specimen length, portions of said cannula adjacent the distal end thereof overlying said side-facing notch when said cannula and stylet are both in said retracted or extended positions and exposing the predetermined length of said notch at the distal end thereof when said cannula and said stylet are in their retracted and extended positions respectively whereby specimens from successive biopsies are stored seriatim in said side-facing notch.

8. A biopsy needle instrument as recited in claim 7 wherein the axial length of said side-facing notch is at least twice the predetermined specimen length.

9. A biopsy needle instrument as recited in claim 7 wherein the axial length of said side-facing notch is at least an integer number of times the predetermined specimen length and said side-facing notch and said side-facing notch stores a number of specimens equal to at least the integer number.

10. A biopsy needle instrument as recited in claim 7 wherein said displacement means extends said stylet and said cannula at a velocity that produces only minimal axial specimen displacement with the moving one of said cannula means and said stylet means.

11. A biopsy needle instrument as recited in claim 7 wherein said distal positions of said stylet and cannula have oppositely beveled ends for facilitating the operation of said instrument.

12. A biopsy needle instrument as recited in claim 11 wherein said cannula means includes marker means at the distal end thereof for facilitating the placement of said instrument.

13. A biopsy needle instrument as recited in claim 11 wherein said cannula means includes distal and proximal sections releasably joined proximally from the position of said side-facing notch and releasable clamping means for joining said sections, said distal section being removable from said instrument to provide access to any specimens stored in said side-facing notch.

14. A biopsy needle instrument as recited in claim 13 wherein said cannula means includes marker means at the distal end thereof for facilitating the placement of said instrument.

15. A method for obtaining, seriatim, multiple biopsy specimens in a biopsy needle instrument including an elongated, side-facing notch formed in a stylet supported within a cannula wherein the stylet and cannula are adapted for independent displacement between retracted and extended positions and the stylet and cannula are in their extended and retracted positions respectively, said method comprising multiple iterations of the steps of:
   A. extending the cannula over the stylet to cover a specimen defined at the distal end of the side-facing notch,
   B. retracting the stylet and cannula,
   C. advancing the stylet independently of the cannula thereby to define a successive specimen and displace previously obtained specimens axially in the notch.

16. A method for obtaining plural specimens as recited in claim 15 wherein said retracting step conditions the instrument extension by displacing the stylet and cannula at a first velocity and said advancing steps produce movement of said stylet and cannula at significantly greater velocities.

17. A method for obtaining plural specimens as recited in claim 16 wherein said advancing steps produce velocities that produce only minimal specimen displacement with the motion of the stylet or cannula.

18. A method for obtaining plural specimens as recited in claim 16 wherein the cannula has a distal portion and a proximal portion, said advancing and retracting steps moving said distal and proximal portions of said cannula simultaneously.

19. A method for obtaining plural specimens as recited in claim 18 additionally comprising the step of removing said distal cannula portion from the stylet for facilitating the removal of the specimens from the stylet.

* * * * *